United States Patent [19]  [11] Patent Number: 4,822,406
Fest et al. [45] Date of Patent: Apr. 18, 1989

[54] O-ARYL-N'-(TRIAZIN-2-YL)-ISOUREA HERBICIDES

[75] Inventors: Christa Fest; Hans-Jochem Riebel, both of Wuppertal; Hans-Joachim Santel, Leverkusen; Robert R. Schmidt, Bergisch Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 105,852

[22] Filed: Oct. 7, 1987

[30] Foreign Application Priority Data

Oct. 14, 1986 [DE] Fed. Rep. of Germany ....... 3634928

[51] Int. Cl.⁴ .................. A01N 43/66; A01N 43/68; C07D 251/46; C07D 251/52
[52] U.S. Cl. ........................... 71/93; 544/211; 544/212; 544/206; 544/207; 544/208; 544/209; 544/197; 544/198; 534/632; 534/751
[58] Field of Search .............. 71/93; 544/211, 206, 544/208, 197, 198, 207, 209, 212; 534/632, 751

[56] References Cited

U.S. PATENT DOCUMENTS 4,310,346 1/1982 Levitt et al. ................. 544/206

Primary Examiner—John M. Ford
Attorney, Agent, or Firm—Sprung Horn Kramer & Woods

[57] ABSTRACT

An O-aryl-N'-(triazin-2-yl)-isourea of the formula

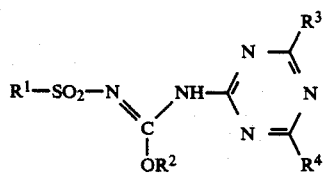

in which
R¹ represents the radical

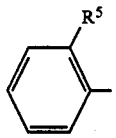

wherein
R⁵ represents trifluoromethoxy, difluoromethoxy, phenyl, phenoxy, trifluoromethylthio, difluoromethylthio, di-(C₁-C₄-alkyl)-aminocarbonyl, C₁-C₄-alkylsulphonyl, C₁-C₄-alkoxyaminosulphonyl, N-(C₁-C₄-alkoxy)-N-(C₁-C₄-alkyl)-aminosulphonyl, C₁-C₄-alkylaminosulphonyl or di-(C₁-C₄-alkyl)-aminosulphonyl,
or wherein
R¹ represents the radical

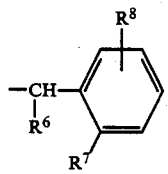

wherein
R⁶ represents hydrogen or C₁-C₄-alkyl and
R⁷ and R⁸ are identical or different and represent hydrogen, fluorine, chlorine, bromine, nitro, cyano, C₁-C₄-alkyl (which is optionally substituted by fluorine and/or chlorine), C₁-C₄-alkoxy (which is optionally substituted by fluorine and/or chlorine), carboxyl, C₁-C₄-alkoxycarbonyl, C₁-C₄-alkylsulphonyl or di-(C₁-C₄-alkyl)-aminosulphonyl;
R² represents optionally substituted aryl,
R³ represents hydrogen, halogen, hydroxyl, C₁-C₆-alkylamino or di-(C₁-C₆-alkyl)-amino, or represents optionally substituted C₁-C₆-alkyl, C₁-C₆-alkoxy or C₁-C₆-alkylthio and
R⁴ respresents hydrogen, halogen or hydroxyl, or represents optionally substituted C₁-C₆-alkyl, C₁-C₆-alkoxy or C₁-C₆-alkylthio, or represents C₁-C₆-alkylamino or di-(C₁-C₆-alkyl)-amino.

6 Claims, No Drawings

O-ARYL-N'-(TRIAZIN-2-YL)-ISOUREA HERBICIDES

The invention relates to new O-aryl-N'-(triazin-2-yl)-isoureas, a process for their preparation and their use as herbicides.

It is known that certain isoureas, such as, for example, N'-(2-chloro-benzenesulphonyl)-N''-(4,6-dimethyl-pyrimidin-2-yl)-O-(4-chlorophenyl)-isourea and N'-(2-chloro-benzenesulphonyl)-N''-(4,6-dimethyl-1,3,5-triazin-2-yl)-O-phenyl-isourea, have herbicidal properties. However, the action of these compounds is not always completely satisfactory (compare, for example, Swiss Patent Specification No. 646,957 and European Patent No. A-173,957).

New O-aryl-N'-(triazin-2-yl)-isoureas of the general formula (I)

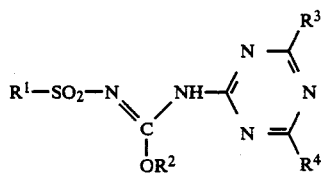  (I)

in which $R^1$ represents the radical

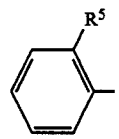

wherein $R^5$ represents trifluoromethoxy, difluoromethoxy, phenyl, phenoxy, trifluoromethylthio, difluoromethylthio, di-($C_1$–$C_4$-alkyl)-aminocarbonyl, $C_1$–$C_4$-alkylsulphonyl, $C_1$–$C_4$-alkoxyaminosulphonyl, N-($C_1$–$C_4$-alkoxy)-N-($C_1$–$C_4$-alkyl)-aminosulphonyl, $C_1$–$C_4$-alkylaminosulphonyl or di-($C_1$–$C_4$-alkyl)-aminosulphonyl, or wherein, furthermore, $R^1$ represents the radical

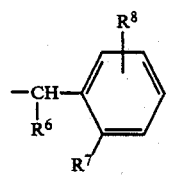

wherein $R^6$ represents hydrogen or $C_1$–$C_4$-alkyl and $R^7$ and $R^8$ are identical or different and represent hydrogen, fluorine, chlorine, bromine, nitro, cyano, $C_1$–$C_4$-alkyl [which is optionally substituted by fluorine and/or chlorine], $C_1$–$C_4$-alkoxy [which is optionally substituted by fluorine and/or chlorine], carboxyl, $C_1$–$C_4$-alkoxycarbonyl, $C_1$–$C_4$-alkylsulphonyl or di-($C_1$–$C_4$-alkyl)-aminosulphonyl;

and wherein, furthermore, $R^2$ represents optionally substituted aryl, $R^3$ represents hydrogen, halogen, hydroxyl, $C_1$–$C_6$-alkylamino or di-($C_1$–$C_6$-alkyl)-amino, or represents optionally substituted $C_1$–$C_6$-alkyl, $C_1$–$C_6$-alkoxy or $C_1$–$C_6$-alkylthio and $R^4$ represents hydrogen, halogen or hydroxyl, or represents optionally substituted $C_1$–$C_6$-alkyl, $C_1$–$C_6$-alkoxy or $C_1$–$C_6$-alkylthio, or represents $C_1$–$C_6$-alkylamino or di-($C_1$–$C_6$-alkyl)-amino, have now been found.

The new O-aryl-N'-(triazin-2-yl)-isoureas of the general formula (I) are obtained by a process in which iminocarbonic acid esters of the formula (II)

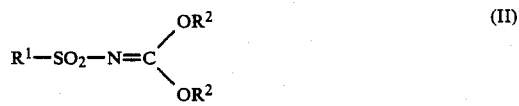  (II)

in which $R^1$ and $R^2$ have the abovementioned meanings, are reacted with 2-amino-triazines of the formula (III)

  (III)

in which $R^3$ and $R^4$ have the abovementioned meanings, in the presence of acid acceptors and if appropriate in the presence of diluents.

The new O-aryl-N'-(triazin-2-yl)-isoureas of the formula (I) are distinguished by a potent herbicidal activity. Surprisingly, the new compounds of the formula (I) exhibit a considerably better herbicidal action than the already known isoureas of the same type of action.

The invention preferably relates to compounds of the formula (I)

in which $R^1$ represents the radical

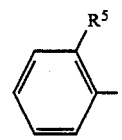

wherein $R^5$ represents trifluoromethoxy, difluoromethoxy, phenyl, phenoxy, trifluoromethylthio, difluoromethylthio, di-($C_1$–$C_4$-alkyl)-aminocarbonyl, $C_1$–$C_3$-alkylsulphonyl, $C_1$–$C_4$-alkoxyaminosulphonyl, N-($C_1$–$C_2$-alkoxy)-N-($C_1$–$C_2$-alkyl)-aminosulphonyl, $C_1$–$C_2$-alkylaminosulphonyl or di-($C_1$–$C_2$-alkyl)-aminosulphonyl, or wherein, furthermore, $R^1$ represents the radical

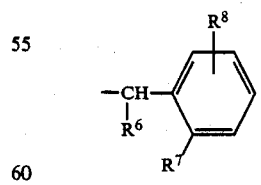

wherein $R^6$ represents hydrogen or $C_1$–$C_4$-alkyl and $R^7$ and $R^8$ are identical or different and represent hydrogen, fluorine, chlorine, bromine, cyano, methyl, methoxy, trifluoromethyl, trifluoromethoxy, difluoromethoxy, carboxyl, methoxycarbonyl, ethoxycarbonyl, methylsulphonyl, ethylsulphonyl, dimethylaminosulphonyl or diethylaminosulphonyl;

and wherein, furthermore, $R^2$ represents a phenyl radical which is optionally substituted by one or more radicals from the series comprising halogen [such as, in particular, fluorine, chlorine, bromine and iodine], cyano, nitro, hydroxyl, carboxyl, $C_1$–$C_6$-alkyl [which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl], $C_3$–$C_6$-cycloalkyl, $C_1$–$C_4$-alkoxy [which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl], $C_1$–$C_4$-alkylthio [which is optionally substituted by fluorine, chlorine, bromine, cyano, carboxyl, $C_1$–$C_4$-alkoxy-carbonyl], amino, $C_1$–$C_4$-alkyl-amino and di-($C_1$–$C_4$-alkyl)amino [which are optionally substituted by fluorine, chlorine, bromine, cyano, carboxyl, $C_1$–$C_4$-alkoxy or $C_1$–$C_4$-alkoxy-carbonyl], $C_1$–$C_4$-alkyl-carbonyl-amino, $C_1$–$C_4$-alkoxycarbonylamino, (di)-$C_1$–$C_4$-alkylamino-carbonylamino, formyl, $C_1$–$C_4$-alkyl-carbonyl, benzoyl, $C_1$–$C_4$-alkoxy-carbonyl, phenoxycarbonyl, benzyloxycarbonyl, phenyl [which is optionally substituted by fluorine, chlorine, bromine, cyano, nitro, hydroxyl or methyl], phenoxy, phenylthio, phenylsulphonyl, phenylamino or phenylazo [which are optionally substituted by fluorine, chlorine, bromine, cyano, nitro, methyl and/or trifluoromethyl], pyridoxy and pyrimidoxy [which are optionally substituted by fluorine, chlorine, bromine, cyano, nitro, methyl and/or trifluoromethyl], $C_1$–$C_4$-alkyl-carbonyloxy, $C_1$–$C_4$-alkoxycarbonyloxy, $C_1$–$C_4$-alkyl-amino-carbonyloxy and di-($C_1$–$C_4$-alkyl)-amino-carbonyloxy, or which is optionally fused with an alkylene chain [which is optionally branched and/or interrupted by one or more oxygen atoms] or a benzo radical [which is optionally substituted by fluorine, chlorine, bromine, cyano, nitro, methyl and/or trifluoromethyl];

and wherein, furthermore, $R^3$ represents hydrogen, fluorine, chlorine, bromine, hydroxyl, $C_1$–$C_4$-alkylamino, di-($C_1$–$C_4$-alkyl)-amino, $C_1$–$C_4$-alkyl [which is optionally substituted by fluorine and/or chlorine], $C_1$–$C_4$-alkoxy [which is optionally substituted by fluorine and/or chlorine] or $C_1$–$C_4$-alkylthio [which is optionally substituted by fluorine and/or chlorine] and $R^4$ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], $C_1$–$C_4$-alkyl-amino or di-($C_1$–$C_4$-alkyl)-amino.

Particularly preferred compounds of the formula (I) are those in which $R^1$ represents the radical

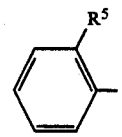

wherein $R^5$ represents difluoromethoxy, trifluoromethoxy, difluoromethylthio, trifluoromethylthio, dimethylaminocarbonyl, diethylaminocarbonyl, di-n-propylaminocarbonyl, methylsulphonyl, ethylsulphonyl, n-propylsulphonyl, i-propylsulphonyl, dimethylaminosulphonyl, diethylaminosulphonyl, methoxyaminosulphonyl, N-methoxy-N-methylaminosulphonyl or phenyl, or represents phenoxy and $R^2$ represents a phenyl radical which is optionally substituted by one or two radicals from the series comprising fluorine, chlorine, bromine, iodine, cyano, nitro, hydroxyl, carboxyl, $C_1$–$C_3$-alkoxy-carbonyl, $C_1$–$C_4$-alkyl, trifluoromethyl, hydroxymethyl, methoxycarbonylmethyl, phenyl-$C_1$–$C_3$-alkyl, cyclohexyl, $C_1$–$C_3$-alkoxy, trifluoromethoxy, $C_1$–$C_3$-alkylthio, trifluoromethylthio, dimethylamino, amino, acetylamino, methylaminocarbonyl, formyl, acetyl, benzoyl, phenyl, hydroxyphenyl, phenoxy [which is optionally substituted by chlorine and/or trifluoromethyl], phenylamino, phenylazo and pyridoxy [which is optionally substituted by chlorine and/or trifluoromethyl], or which is optionally benzo-fused;

and wherein, furthermore, $R^3$ represents fluorine, chlorine, methyl, ethyl, methoxy, ethoxy, methylthio, ethylthio, methylamino, ethylamino, dimethylamino or diethylamino and $R^4$ represents fluorine, chlorine, methyl, ethyl, methoxy, ethoxy, methylthio, ethylthio, methylamino, ethylamino, dimethylamino or diethylamino.

If, for example, O,O-diphenyl N-(2-trifluoromethoxybenzenesulphonyl)-iminocarbonate and 2-amino-4-methoxy-6-methyl-1,3,5-triazine are used as starting substances for the process according to the invention, the course of the reaction can be illustrated by the following equation:

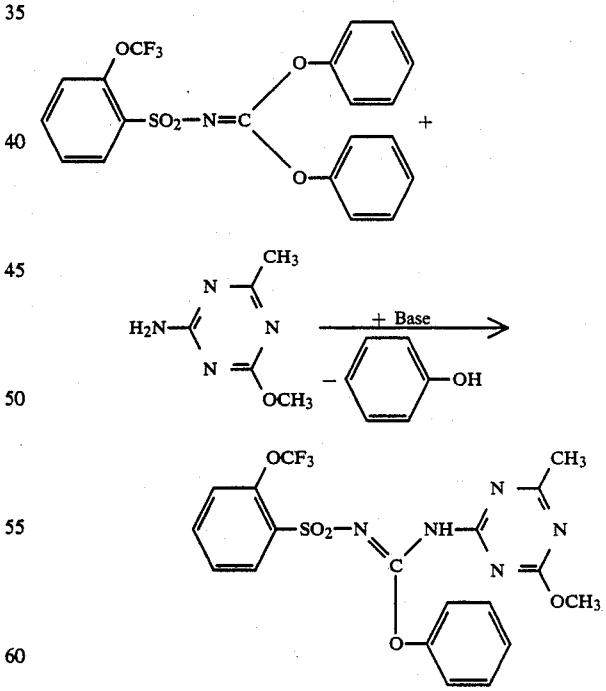

Formula (II) provides a general definition of the iminocarbonic acid esters to be used as starting substances in the process according to the invention. In this formula (II), $R^1$ and $R^2$ preferably represent those radicals which have already been mentioned as preferred for these substituents in connection with the description of the substances of the formula (I) according to the invention.

The compounds of the formula (II) are new and are the subject of Application Ser. No. 105859 (corresponding to German Application No. P 36 34 926.7, Bayer 6925) being filed simultaneously herewith and does not belong to the previously published prior art.

The compounds of the formula (II) are obtained by a process in which iminocarbonic acid dichlorides of the formula (IV)

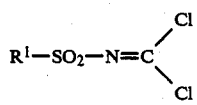

in which $R^1$ has the abovementioned meanings, are reacted with compounds of the formula (V)

$R^2$—OM     (V)

in which
$R^2$ has the abovementioned meanings and
M represents hydrogen or an alkali metal atom, if appropriate in the presence of acid acceptors, such as, for example, sodium hydroxide or potassium hydroxide, and if appropriate in the presence of inert diluents, such as, for example, acetone, methyl ethyl ketone or acetonitrile, at temperatures between 10° C. and 100° C.

The iminocarbonic acid dichlorides of the formula (IV) are new. They are likewise the subject of Application Ser. No. 105859 filed 10-7-87 (corresponding to German Application No. P 36 34 926.7).

The new compounds of the formula (IV) are obtained by a process in which dimethyl iminodithiocarbonates of the formula (VI)

in which $R^1$ has the abovementioned meanings, are reacted with chlorinating agents, such as, for example, sulphuryl chloride or chlorine, in the presence of inert diluents, such as, for example, carbon tetrachloride, at temperatures between 0° C. and 25° C.

The dimethyl iminodithiocarbonates of the formula (VI) are known and/or can be prepared by known methods (compare, for example, European Pat. No. A-121,082, European Pat. No. A-151,554 and European Pat. No. A-173,957).

The compounds of the formula (V) furthermore to be used as starting substances for the preparation of the compounds of the formula (II) are generally known compounds of organic chemistry.

Examples which may be mentioned of the iminocarbonic acid esters of the formula (II) are:

TABLE 1

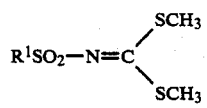

| $R^1$ | $R^2$ |
|---|---|
| 2-OCF$_3$-phenyl | phenyl |
| 2-OCF$_3$-phenyl | 4-Cl-phenyl |
| 2-OCF$_3$-phenyl | 2-Cl-phenyl |
| 2-OCF$_3$-phenyl | 3-Cl-phenyl |
| 2-OCF$_3$-phenyl | 4-CH$_3$-phenyl |
| 2-OCF$_3$-phenyl | 2-CH$_3$-phenyl |
| 2-OCF$_3$-phenyl | 3-CH$_3$-phenyl |
| 2-OCF$_3$-phenyl | 4-HO-phenyl |
| 2-OCF$_3$-phenyl | 4-tert.-C$_4$H$_9$-phenyl |
| 2-OCF$_3$-phenyl | 4-C$_2$H$_5$-phenyl |

TABLE 1-continued $$R^1-SO_2-N=C{\overset{\displaystyle OR^2}{\underset{\displaystyle OR^2}{}}} \quad (II)$$

| R¹ | R² |
|---|---|
| 2-OCF₃-C₆H₄- | 2-C₂H₅-C₆H₄- |
| 2-OCF₃-C₆H₄- | 3-C₂H₅-C₆H₄- |
| 2-OCF₃-C₆H₄- | 2-Br-C₆H₄- |
| 2-OCF₃-C₆H₄- | 3-Br-C₆H₄- |
| 2-OCF₃-C₆H₄- | 4-Br-C₆H₄- |
| 2-OCF₃-C₆H₄- | 2-naphthyl |
| 2-OCF₃-C₆H₄- | 2-OCH₃-C₆H₄- |
| 2-OCF₃-C₆H₄- | 3-OCH₃-C₆H₄- |
| 2-OCF₃-C₆H₄- | 4-OCH₃-C₆H₄- |
| 2-OCF₃-C₆H₄- | 2-OC₂H₅-C₆H₄- |
| 2-OCF₃-C₆H₄- | 3-OC₂H₅-C₆H₄- |
| 2-OCF₃-C₆H₄- | 4-OC₂H₅-C₆H₄- |
| 2-OCF₃-C₆H₄- | 2,4-Cl₂-C₆H₃- |
| 2-OCF₃-C₆H₄- | 2,6-Cl₂-C₆H₃- |
| 2-OCF₃-C₆H₄- | 2-OC₃H₇-n-C₆H₄- |
| 2-OCF₃-C₆H₄- | 3-OC₃H₇-n-C₆H₄- |
| 2-OCF₃-C₆H₄- | 4-OC₃H₇-n-C₆H₄- |
| 2-OCF₃-C₆H₄- | 4-SCH₃-C₆H₄- |
| 2-OCF₃-C₆H₄- | 3-N(CH₃)₂-C₆H₄- |
| 2-OCF₃-C₆H₄- | 2-F-C₆H₄- |

TABLE 1-continued $$R^1-SO_2-N=C\begin{matrix}OR^2\\OR^2\end{matrix} \quad (II)$$

| R¹ | R² |
|---|---|
| 2-(OCF₃)phenyl | 4-F-phenyl |
| 2-(OCF₃)phenyl | 4-phenoxyphenyl |
| 2-(OCHF₂)phenyl | phenyl |
| 2-(OCHF₂)phenyl | 4-Cl-phenyl |
| 2-(OCHF₂)phenyl | 2-Cl-phenyl |
| 2-(OCHF₂)phenyl | 3-Cl-phenyl |
| 2-(OCHF₂)phenyl | 4-CH₃-phenyl |
| 2-(OCHF₂)phenyl | 2-CH₃-phenyl |
| 2-(OCHF₂)phenyl | 3-CH₃-phenyl |
| 2-(OCHF₂)phenyl | 4-HO-phenyl |
| 2-(OCHF₂)phenyl | 4-tert.-C₄H₉-phenyl |
| 2-(OCHF₂)phenyl | 4-C₂H₅-phenyl |
| 2-(OCHF₂)phenyl | 2-C₂H₅-phenyl |
| 2-(OCHF₂)phenyl | 3-C₂H₅-phenyl |
| 2-(OCHF₂)phenyl | 2-Br-phenyl |
| 2-(OCHF₂)phenyl | 3-Br-phenyl |
| 2-(OCHF₂)phenyl | 4-Br-phenyl |
| 2-(OCHF₂)phenyl | 2-naphthyl |
| 2-(OCHF₂)phenyl | 2-OCH₃-phenyl |
| 2-(OCHF₂)phenyl | 3-OCH₃-phenyl |

TABLE 1-continued $$R^1-SO_2-N=C\begin{matrix}OR^2\\OR^2\end{matrix} \quad (II)$$

| $R^1$ | $R^2$ |
|---|---|
| 2-(OCHF₂)phenyl | 4-(H₃CO)phenyl |
| 2-(OCHF₂)phenyl | 2-(OC₂H₅)phenyl |
| 2-(OCHF₂)phenyl | 3-(H₅C₂O)phenyl |
| 2-(OCHF₂)phenyl | 4-(H₅C₂O)phenyl |
| 2-(OCHF₂)phenyl | 2,4-dichlorophenyl |
| 2-(OCHF₂)phenyl | 2,6-dichlorophenyl |
| 2-(OCHF₂)phenyl | 2-(OC₃H₇-n)phenyl |
| 2-(OCHF₂)phenyl | 3-(n-H₇C₃O)phenyl |
| 2-(OCHF₂)phenyl | 4-(n-H₇C₃O)phenyl |
| 2-(OCHF₂)phenyl | 4-(H₃CS)phenyl |
| 2-(OCHF₂)phenyl | 3-(N(CH₃)₂)phenyl |
| 2-(OCHF₂)phenyl | 2-fluorophenyl |
| 2-(OCHF₂)phenyl | 4-fluorophenyl |
| 2-(OCHF₂)phenyl | 4-phenoxyphenyl |
| 2-biphenyl | phenyl |
| 2-biphenyl | 4-chlorophenyl |
| 2-biphenyl | 2-chlorophenyl |
| 2-biphenyl | 3-chlorophenyl |

TABLE 1-continued $$R^1-SO_2-N=C\begin{matrix}OR^2\\OR^2\end{matrix} \quad (II)$$

| R¹ | R² |
|---|---|
| 2-biphenylyl | 4-methylphenyl |
| 2-biphenylyl | 2-methylphenyl |
| 2-biphenylyl | 3-methylphenyl |
| 2-biphenylyl | 4-hydroxyphenyl |
| 2-biphenylyl | 4-tert-butylphenyl |
| 2-biphenylyl | 4-ethylphenyl |
| 2-biphenylyl | 2-ethylphenyl |
| 2-biphenylyl | 3-ethylphenyl |
| 2-biphenylyl | 2-bromophenyl |
| 2-biphenylyl | 3-bromophenyl |
| 2-biphenylyl | 4-bromophenyl |
| 2-biphenylyl | 2-naphthyl |

TABLE 1-continued
$$R^1-SO_2-N=C\begin{matrix}OR^2\\OR^2\end{matrix} \quad (II)$$
| $R^1$ | $R^2$ |
|---|---|
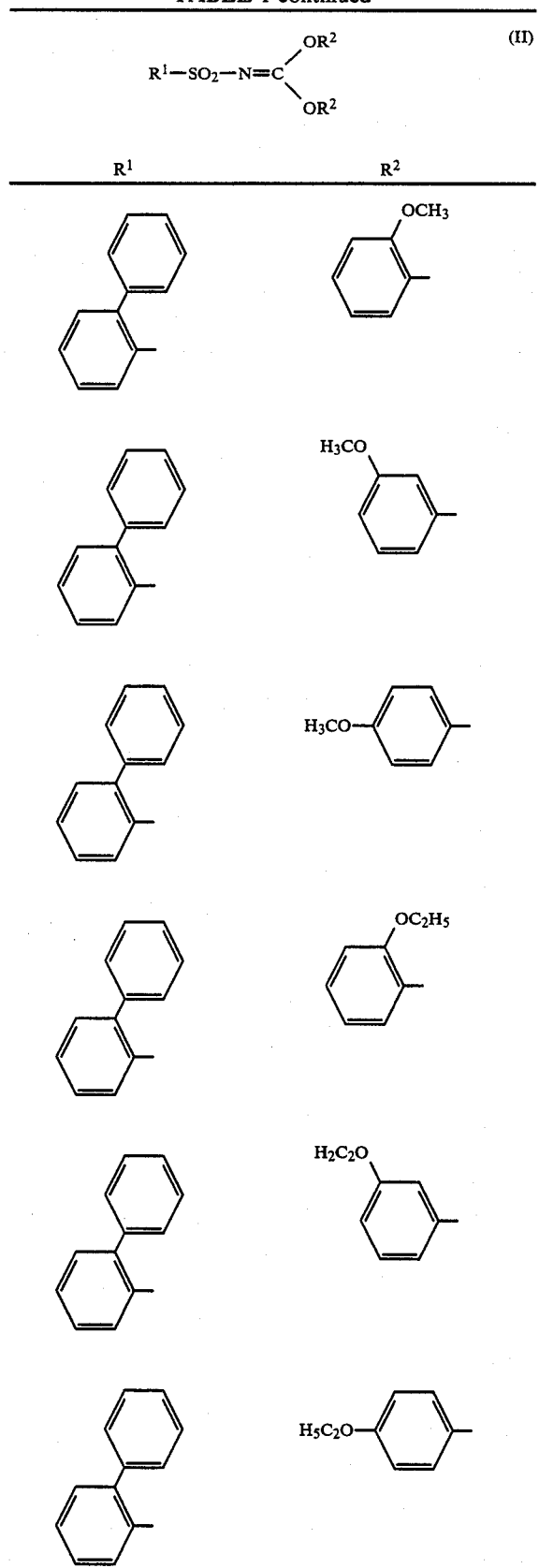
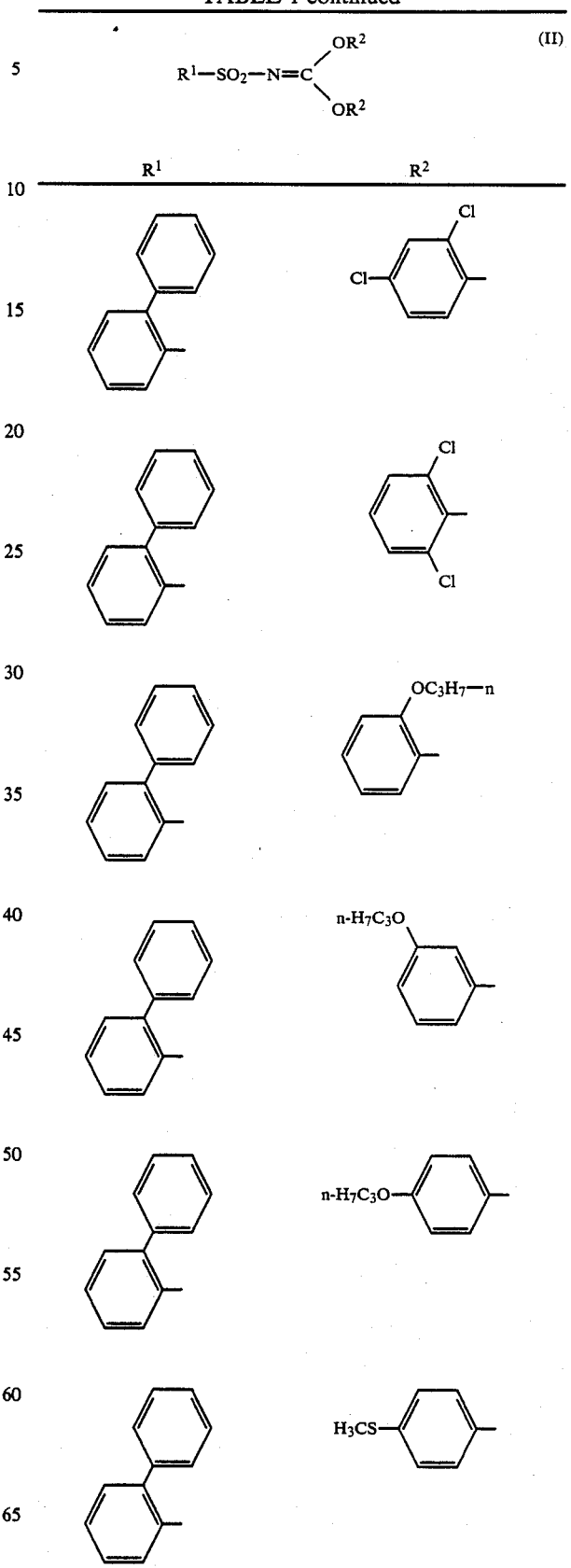

TABLE 1-continued
$$R^1-SO_2-N=C\begin{matrix}OR^2\\OR^2\end{matrix} \quad (II)$$
| R¹ | R² |
|---|---|
| 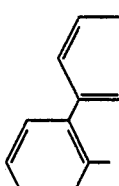 | 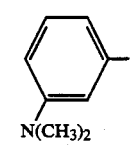 |
| 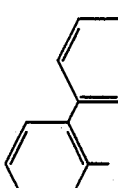 | 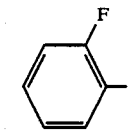 |
| 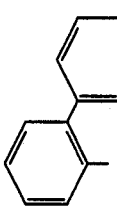 | 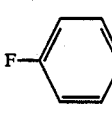 |
| 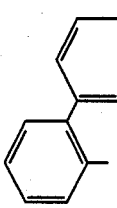 | 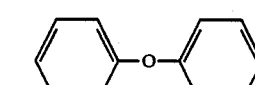 |
| 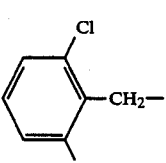 | 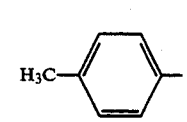 |
| 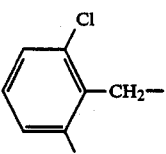 | 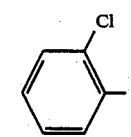 |
| 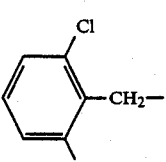 | 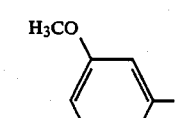 |
| 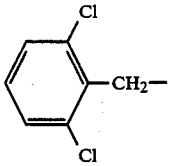 | 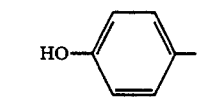 |
| 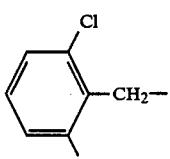 | 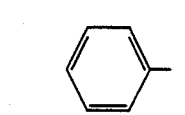 |
| 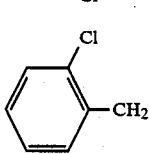 |  |
| 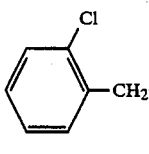 | 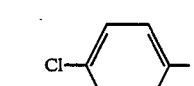 |
| 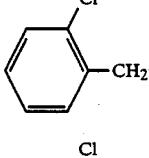 | 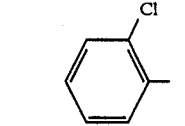 |
| 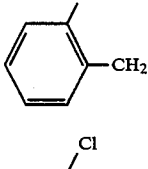 | 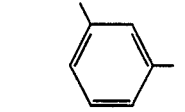 |
| 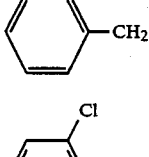 | 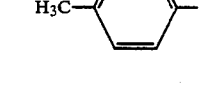 |
| 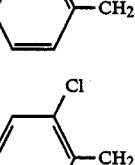 | 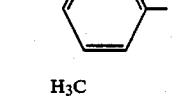 |

TABLE 1-continued $$R^1-SO_2-N=C\begin{matrix}OR^2\\OR^2\end{matrix} \quad (II)$$

| $R^1$ | $R^2$ |
|---|---|
| 2-Cl-C6H4-CH2- | 4-tert.-C4H9-C6H4- |
| 2-Cl-C6H4-CH2- | 4-C2H5-C6H4- |
| 2-Cl-C6H4-CH2- | 2-C2H5-C6H4- |
| 2-Cl-C6H4-CH2- | 3-C2H5-C6H4- |
| 2-Cl-C6H4-CH2- | 2-Br-C6H4- |
| 2-Cl-C6H4-CH2- | 3-Br-C6H4- |
| 2-Cl-C6H4-CH2- | 4-Br-C6H4- |
| 2-Cl-C6H4-CH2- | 2-naphthyl |
| 2-Cl-C6H4-CH2- | 2-OCH3-C6H4- |
| 2-Cl-C6H4-CH2- | 3-OCH3-C6H4- |
| 2-Cl-C6H4-CH2- | 4-OCH3-C6H4- |
| 2-Cl-C6H4-CH2- | 2-OC2H5-C6H4- |
| 2-Cl-C6H4-CH2- | 3-OCH2-C6H4- |
| 2-Cl-C6H4-CH2- | 4-OC2H5-C6H4- |
| 2-Cl-C6H4-CH2- | 2,4-di-Cl-C6H3- |
| 2-Cl-C6H4-CH2- | 2,6-di-Cl-C6H3- |
| 2-Cl-C6H4-CH2- | 2-OC3H7-n-C6H4- |
| 2-Cl-C6H4-CH2- | 3-O-n-C3H7-C6H4- |
| 2-Cl-C6H4-CH2- | 4-O-n-C3H7-C6H4- |
| 2-Cl-C6H4-CH2- | 4-SCH3-C6H4- |

TABLE 1-continued $$R^1-SO_2-N=C\begin{smallmatrix}OR^2\\OR^2\end{smallmatrix} \quad (II)$$

| R¹ | R² |
|---|---|
| 2-Cl-benzyl (-CH₂-C₆H₄-Cl) | 3-N(CH₃)₂-phenyl |
| 2-Cl-benzyl | 2-F-phenyl |
| 2-Cl-benzyl | 4-F-phenyl |
| 2-Cl-benzyl | 4-phenoxyphenyl |
| 2-CO-N(CH₃)₂-phenyl | 2-Cl-phenyl |
| 2-CO-N(CH₃)₂-phenyl | 3-H₃CO-phenyl |
| 2-CO-N(CH₃)₂-phenyl | 4-HO-phenyl |
| 2-CO-N(CH₃)₂-phenyl | phenyl |
| 2-SO₂N(CH₃)₂-phenyl | 4-H₃C-phenyl |
| 2-SO₂N(CH₃)₂-phenyl | 2-Cl-phenyl |
| 2-SO₂N(CH₃)₂-phenyl | 3-H₃CO-phenyl |
| 2-SO₂N(CH₃)₂-phenyl | 4-HO-phenyl |
| 2-SO₂N(CH₃)₂-phenyl | phenyl |
| 2-phenoxyphenyl | phenyl |
| 2-phenoxyphenyl | 4-Cl-phenyl |
| 2-phenoxyphenyl | 2-Cl-phenyl |
| 2-phenoxyphenyl | 3-Cl-phenyl |
| 2-phenoxyphenyl | 4-H₃C-phenyl |

TABLE 1-continued
$$R^1-SO_2-N=C\begin{matrix}OR^2\\OR^2\end{matrix} \quad (II)$$
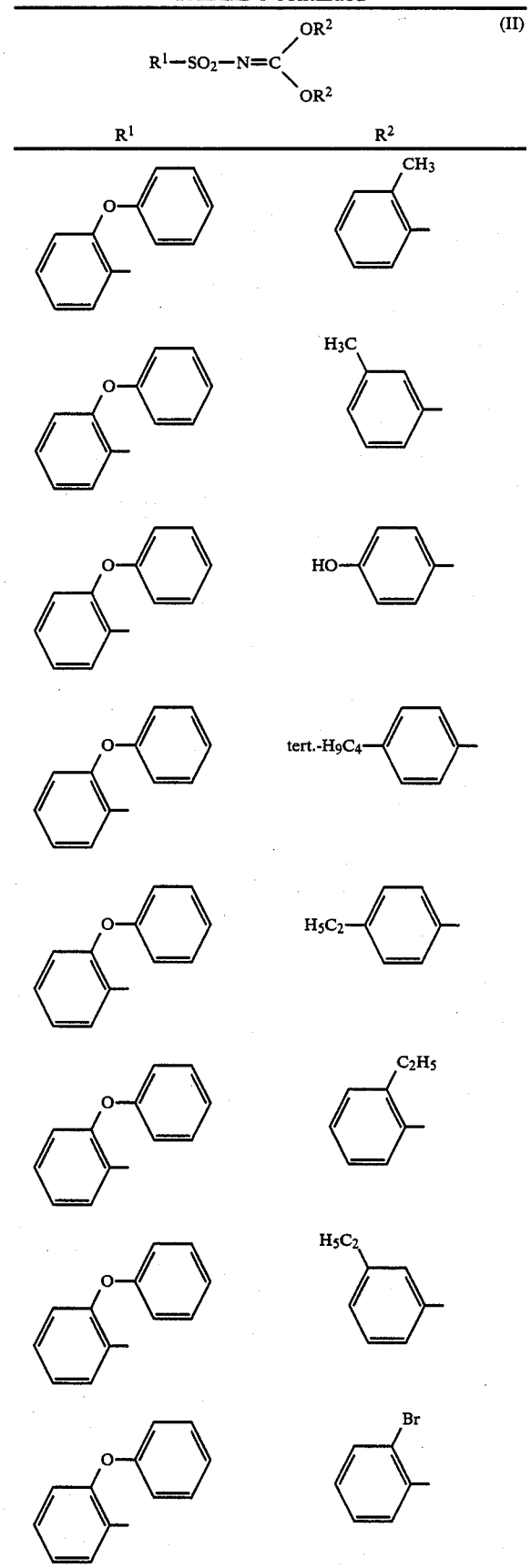
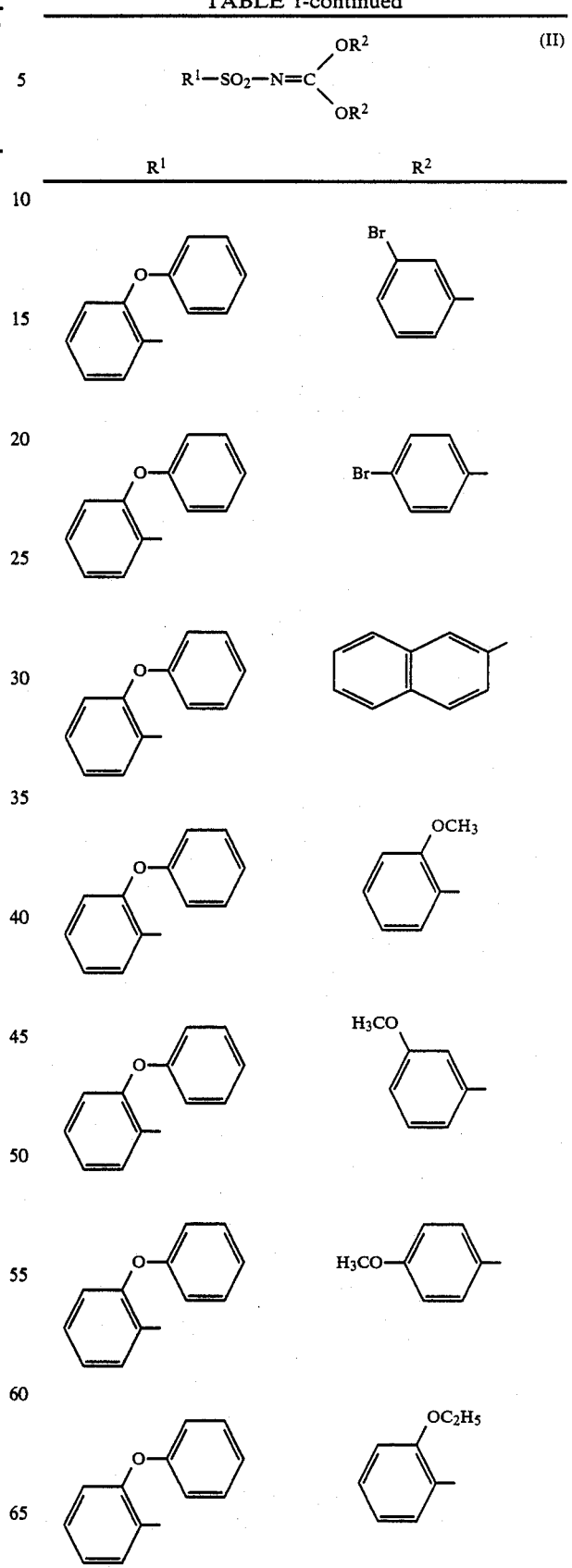

TABLE 1-continued $$R^1-SO_2-N=C\begin{matrix}OR^2\\OR^2\end{matrix} \quad (II)$$

| R¹ | R² |
|---|---|
| 2-phenoxyphenyl | 3-ethoxyphenyl (H₅C₂O-) |
| 2-phenoxyphenyl | 4-ethoxyphenyl (H₅C₂O-) |
| 2-phenoxyphenyl | 2,4-dichlorophenyl |
| 2-phenoxyphenyl | 2,6-dichlorophenyl |
| 2-phenoxyphenyl | 2-(n-propoxy)phenyl (OC₃H₇-n) |
| 2-phenoxyphenyl | 3-(n-propoxy)phenyl (n-H₇C₃O-) |
| 2-phenoxyphenyl | 4-(n-propoxy)phenyl (n-H₇C₃O-) |
| 2-phenoxyphenyl | 4-(methylthio)phenyl (H₃CS-) |
| 2-phenoxyphenyl | 3-(dimethylamino)phenyl (N(CH₃)₂) |
| 2-phenoxyphenyl | 2-fluorophenyl (F) |
| 2-phenoxyphenyl | 4-fluorophenyl (F-) |
| 2-phenoxyphenyl | 4-phenoxyphenyl |

Formula (III) provides a general definition of the 2-amino-triazines also to be used as starting substances in the process according to the invention. In this formula (III), $R^3$ and $R^4$ preferably represent those radicals which have already been mentioned as preferred for these substituents in connection with the description of the substances of the formula (I) according to the invention.

Examples which may be mentioned of the 2-amino-triazines of the formula (III) are:

TABLE 2

$$\begin{matrix} & & R^3 \\ & N & \\ H_2N-\overset{\|}{C} & & N \\ & N & \\ & & R^4 \end{matrix} \quad (III)$$

| R³ | R⁴ |
|---|---|
| CH₃ | CH₃ |
| OCH₃ | OCH₃ |
| CH₃ | OCH₃ |
| C₂H₅ | C₂H₅ |
| OC₂H₅ | OC₂H₅ |
| OC₂H₅ | CH₃ |
| OC₂H₅ | OCH₃ |
| CH₃ | SCH₃ |
| CH₃ | SC₂H₅ |
| OCH₃ | SCH₃ |

TABLE 2-continued $$\text{H}_2\text{N}-\underset{N=\underset{R^4}{\Big\backslash}}{\overset{N-\underset{R^3}{\Big\nearrow}}{\Big\langle}} \quad \text{(III)}$$

| $R^3$ | $R^4$ |
|---|---|
| OC$_2$H$_5$ | SCH$_3$ |
| OCH$_3$ | SC$_2$H$_5$ |
| OC$_2$H$_5$ | SC$_2$H$_5$ |
| CH$_3$ | NHCH$_3$ |
| CH$_3$ | N(CH$_3$)$_2$ |
| CH$_3$ | NHC$_2$H$_5$ |
| CH$_3$ | N(C$_2$H$_5$)$_2$ |
| OCH$_3$ | NHCH$_3$ |
| OCH$_3$ | NHC$_2$H$_5$ |
| OCH$_3$ | N(CH$_3$)$_2$ |
| OCH$_3$ | N(C$_2$H$_5$)$_2$ |
| OC$_2$H$_5$ | N(C$_2$H$_5$)$_2$ |
| OC$_2$H$_5$ | N(CH$_3$)$_2$ |
| SCH$_3$ | NHCH$_3$ |
| SCH$_3$ | N(CH$_3$)$_2$ |
| SCH$_3$ | NHC$_2$H$_5$ |
| SCH$_3$ | N(C$_2$H$_5$)$_2$ |
| SC$_2$H$_5$ | NHCH$_3$ |
| SC$_2$H$_5$ | N(CH$_3$)$_2$ |
| OC$_2$H$_5$ | NHCH$_3$ |
| OC$_2$H$_5$ | NHC$_2$H$_5$ |
| SC$_2$H$_5$ | N(C$_2$H$_5$)$_2$ |
| Cl | CH$_3$ |

The 2-aminotriazines of the formula (III) are known and/or can be prepared by processes which are known per se.

The process according to the invention for the preparation of the new compounds of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethyl sulphoxide, tetramethylene sulphone and hexamethylphosphoric acid triamide.

Acid acceptors which are used for the process according to the invention for the preparation of the new compounds of the formula (I) are all the acid-binding agents which can usually be employed for such reactions. Preferred possible acid-binding agents are alkali metal hydroxides, such as, for example, sodium hydroxide and potassium hydroxide, alkali metal hydrides, such as, for example, sodium hydride, alkaline earth metal hydroxides, such as, for example, calcium hydroxide, and alkali metal carbonates and alcoholates, such as sodium carbonate, potassium carbonate, sodium methylate or ethylate, potassium methylate or ethylate or potassium tert.-butylate.

The reactions are in general carried out at temperatures between −20° C. and 150° C., preferably at temperatures between 0° C. and 80° C. The reactions are in general carried out under normal pressure.

For carrying out the process according to the invention, the starting substances of the formulae (II) and (III) and, if appropriate, the suitable acid acceptor are employed in equimolar amounts.

Preferably, a compound of the formula (III), the acid acceptor and the diluent, such as, for example, tetrahydrofuran, are taken and are stirred for a few hours. The compound of the formula (II) is then added. After the reaction, the reaction solution is concentrated, water is added and the mixture is filtered with suction over silica gel and rendered weakly acid with a mineral acid, such as, for example, hydrochloric acid. The solution is taken up in an organic diluent, such as, for example, methylene chloride. The organic phase is washed with saturated sodium carbonate solution and then with water, dried and concentrated. The crude products are purified by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The new active compounds are suitable for selectively combating mono- and dicotyledon weeds, in particular in monocotyledon crops, such as, for example, wheat, by the pre- and post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 2-chloro-N-{[(4-methoxy-6-methyl-1,3,5-triazin-2-yl)-amino]-carbonyl}-benzenesulphonamide, 2-hydroxycarbonyl-N-{[(4-methoxy-6-methyl-1,3,5-triazin-2-yl)-amino]-carbonyl}-benzenesulphonamide, 2-ethylamino-6-(1,1-dimethylethyl-amino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H, 3H)-dione, methyl 3-(2,4-dichloro-phenoxy)-6-nitro-benzoate, methyl 2-[4-(2,4-dichlorophenoxy)-phenoxy]-propionate, the R-enantiomer of (trimethylsilyl)-methyl 2-{4-[(3,5-dichloro-2-pyridinyl)-oxy]-phenoxy}-propionate, 2,4-dichlorophenoxyacetic acid, 2-(2,4-dichlorophenoxy)-propionic acid, 4-chloro-2-methylphenoxy-acetic acid, 2-(4-chloro-2-methylphenoxy)-propionic acid, 3,5-diiodo-4-hydroxy-benzonitrile, 3,5-dibromo-4-hydroxy-benzonitrile, N-(1-ethylpropyl)-3,4-dimethyl-2,6-dinitroaniline, 2,3,3-trichloroallyl N,N-diisopropyl-thiolcarbamate, 2-(2-benzothiazolyloxy)-N-methyl-N-phenylacetamide, methyl 2-[4,5-dihydro-4-methyl-4-(1-methylethyl)-5-oxo-1H-imidazol-2-yl]-4(5)-methyl-benzoate, [(4-amino-3,5-dichloro-6-fluoro-2-pyridyl)-oxy]-acetic acid and 3-isopropyl-2,1,3-benzothiadiazin-4-one 2,2-dioxide. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

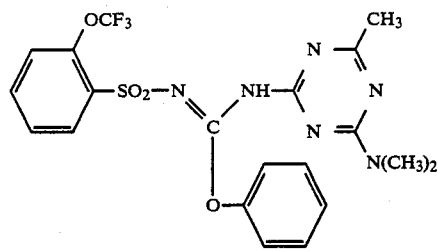

4.1 g (0.027 mol) of 2-amino-4-dimethylamino-6-methyl-1,3,5-triazine are dissolved in 100 ml of tetrahydrofuran, 3.2 g (0.029 mol) of potassium tert.-butylate are added and the mixture is stirred at 20° C. for 2 hours. 11.8 g (0.027 mol) of O,O-diphenyl N-(2-trifluoromethoxy-benzenesulphonyl)-iminocarbonate are then added at 20° C. The reaction mixture is further stirred at 20° C. for about 15 hours and then poured onto 500 ml of ice water and filtered, and the filtrate is acidified with 2N hydrochloric acid and extracted with methylene chloride. The organic phase is washed, dried and concentrated in vacuo. The residue is recrystallized from isopropanol.

9.9 g (73.9% of theory) of N'-(4-dimethylamino-6-methyl-1,3,5-triazin-2-yl)-N"-(2-trifluoromethoxybenzenesulphonyl)-O-phenyl-isourea of melting point 129° C. are obtained.

EXAMPLE 2

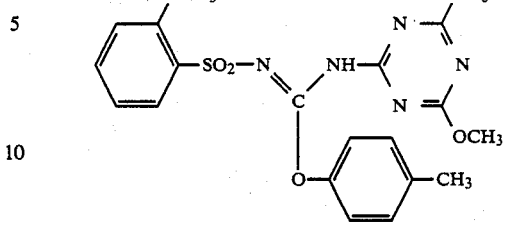

A mixture of 5 g (0.035 mol) of 2-amino-4-methoxy-6-methyl-1,3,5-triazine, 2.4 g (0.07 mol) of sodium hydride in paraffin and 100 ml of tetrahydrofuran is stirred at 25° C. for 15 hours. 15.8 g (0.035 mol) of O,O-di-(4-methyl-phenyl) N-(2-trifluoromethoxybenzenesulphonyl)-iminocarbonate are then added to the mixture in portions so that a temperature of 30° C. is not exceeded, and the mixture is stirred at 25° C. for 3 hours. Thereafter, 300 ml of water are added to the reaction mixture, while cooling with ice. The aqueous phase is brought to a pH of about 5 with dilute hydrochloric acid, washed twice with water, dried over sodium sulphate and concentrated. After incipient distillation (bath temperature: 140° C., 200 Pa), the residue is triturated with ethanol, filtered off and dried.

6.5 g (36% of theory) of N'-(4-methoxy-6-methyl-1,3,5-triazin-2-yl)-N"-(2-trifluoromethoxybenzenesulphonyl)-O-(4-methyl-phenyl)-isourea are obtained in the form of a waxy substance.

The following compounds of the formula (I) can be prepared analogously to Example 1 and 2:

TABLE 3

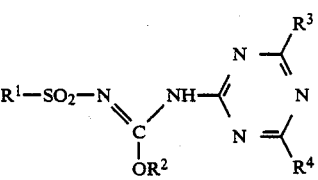

| Example No. | $R^1$ | $R^2$ | $R^3$ | $R^4$ | Melting point/[°C.] |
|---|---|---|---|---|---|
| 3 | 2-OCF$_3$-C$_6$H$_4$- | C$_6$H$_5$- | CH$_3$ | CH$_3$ | 149 |
| 4 | 2-OCF$_3$-C$_6$H$_4$- | 4-O$_2$N-C$_6$H$_4$- | CH$_3$ | CH$_3$ | |
| 5 | 2-Cl-C$_6$H$_4$-CH$_2$- | C$_6$H$_5$- | CH$_3$ | CH$_3$ | 153 |

TABLE 3-continued
$$R^1-SO_2-N=C(OR^2)-NH-\text{triazine}(R^3, R^4) \tag{I}$$
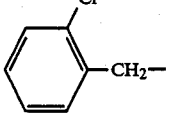
| Example No. | R¹ | R² | R³ | R⁴ | Melting point/[°C.] |
|---|---|---|---|---|---|
| 6 | 2-Cl-C₆H₄-CH₂- | C₆H₅- | CH₃ | OCH₃ | 144 |
| 7 | 2,6-Cl₂-C₆H₃-CH₂- | C₆H₅- | CH₃ | CH₃ | 182 |
| 8 | 2-Cl-C₆H₄-CH₂- | 4-O₂N-C₆H₄- | CH₃ | CH₃ | 176 |
| 9 | 2-Cl-C₆H₄-CH₂- | C₆H₅- | CH₃ | OCH₃ | 143 |
| 10 | 2-Cl-C₆H₄-CH₂- | 4-O₂N-C₆H₄- | CH₃ | OCH₃ | 162 |
| 11 | 2,6-Cl₂-C₆H₃-CH₂- | C₆H₅- | CH₃ | OCH₃ | 168 |
| 12 | 2-Cl-C₆H₄-CH₂- | 4-O₂N-C₆H₄- | OCH₃ | OCH₃ | 171 |
| 13 | 2,6-Cl₂-C₆H₃-CH₂- | 4-O₂N-C₆H₄- | CH₃ | CH₃ | 198 |
| 14 | 2-OCF₃-C₆H₄- | C₆H₅- | CH₃ | SCH₃ | 83 |

TABLE 3-continued $$R^1-SO_2-N=C(OR^2)-NH-\text{triazine}(R^3, R^4) \quad (I)$$

| Example No. | R¹ | R² | R³ | R⁴ | Melting point/[°C.] |
|---|---|---|---|---|---|
| 15 | 2-OCF₃-phenyl | phenyl | Cl | CH₃ | 132 |
| 16 | 2-OCF₃-phenyl | 2,3-diCl-phenyl | OCH₃ | OCH₃ | 131 |
| 17 | 2-OCF₃-phenyl | 2,3-diCl-phenyl | CH₃ | SCH₃ | 157 |
| 18 | 2-OCF₃-phenyl | phenyl | CH₃ | OCH₃ | 76 |
| 19 | 2-OCF₃-phenyl | 3-NO₂-phenyl | OCH₃ | OCH₃ | 152 |
| 20 | 2-OCF₃-phenyl | phenyl | OCH₃ | OCH₃ | 111 |
| 21 | 2-OCF₃-phenyl | 2-CH₃-phenyl | CH₃ | OCH₃ | 127 |
| 22 | 2-OCF₃-phenyl | 3-CH₃-phenyl | CH₃ | OCH₃ | 104 |

TABLE 3-continued
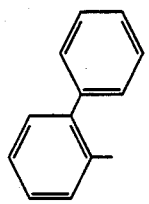
(I)
| Example No. | R¹ | R² | R³ | R⁴ | Melting point/[°C.] |
|---|---|---|---|---|---|
| 23 | 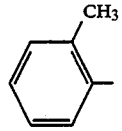 | 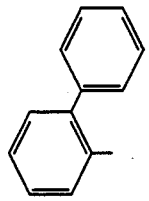 | CH₃ | OCH₃ | |
| 24 | 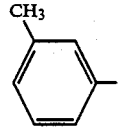 | 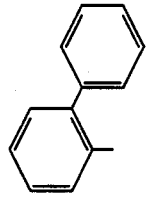 | CH₃ | OCH₃ | |
| 25 | 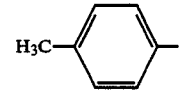 | 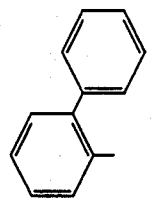 | CH₃ | OCH₃ | 139 |
| 26 | 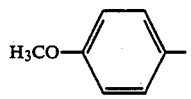 | 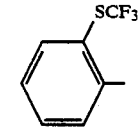 | CH₃ | OCH₃ | |
| 27 | 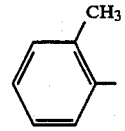 | 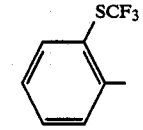 | CH₃ | OCH₃ | |
| 28 | 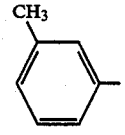 | 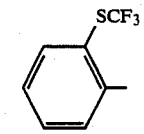 | CH₃ | OCH₃ | |
| 29 | 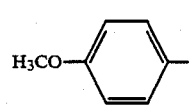 |  | CH₃ | OCH₃ | |

TABLE 3-continued $$R^1-SO_2-N=C(OR^2)-NH-\underset{N=}{\overset{N=}{\bigcirc}}\text{triazine}(R^3, R^4)$$ (I)

| Example No. | R¹ | R² | R³ | R⁴ | Melting point/[°C.] |
|---|---|---|---|---|---|
| 30 | 2-(OCHF₂)-phenyl | 2-methylphenyl | CH₃ | OCH₃ | |
| 31 | 2-(OCHF₂)-phenyl | 3-methylphenyl | CH₃ | OCH₃ | |
| 32 | 2-(OCHF₂)-phenyl | 4-methoxyphenyl | CH₃ | OCH₃ | |
| 33 | 2-[SO₂N(CH₃)₂]-phenyl | 3-methylphenyl | CH₃ | OCH₃ | |
| 34 | 2-[SO₂N(CH₃)₂]-phenyl | 4-methoxyphenyl | CH₃ | OCH₃ | |
| 35 | 2-[SO₂N(OCH₃)(CH₃)]-phenyl | 2-methylphenyl | CH₃ | OCH₃ | |
| 36 | 2-[SO₂N(OCH₃)(CH₃)]-phenyl | 3-methylphenyl | CH₃ | OCH₃ | |
| 37 | 2-[SO₂N(OCH₃)(CH₃)]-phenyl | 4-methoxyphenyl | CH₃ | OCH₃ | |
| 38 | 2-(SO₂CH₃)-phenyl | 2-methylphenyl | CH₃ | OCH₃ | |

TABLE 3-continued $$R^1-SO_2-N=C(OR^2)-NH-\text{[triazine with }R^3, R^4\text{]}$$ (I)

| Example No. | R¹ | R² | R³ | R⁴ | Melting point/[°C.] |
|---|---|---|---|---|---|
| 39 | 2-(SO₂CH₃)C₆H₄− | 3-CH₃−C₆H₄− | CH₃ | OCH₃ | |
| 40 | 2-(SO₂CH₃)C₆H₄− | 4-(H₃CO)C₆H₄− | CH₃ | OCH₃ | |
| 41 | 2-(SO₂C₂H₅)C₆H₄− | 3-CH₃−C₆H₄− | CH₃ | OCH₃ | |
| 42 | 2-(SO₂C₂H₅)C₆H₄− | 3-CH₃−C₆H₄− | CH₃ | OCH₃ | |
| 43 | 2-(SO₂C₂H₅)C₆H₄− | 4-(H₃CO)C₆H₄− | CH₃ | OCH₃ | |
| 44 | 2-(CON(CH₃)₂)C₆H₄− | 3-CH₃−C₆H₄− | CH₃ | OCH₃ | |
| 45 | 2-(CON(CH₃)₂)C₆H₄− | 3-CH₃−C₆H₄− | CH₃ | OCH₃ | |
| 46 | 2-(CON(CH₃)₂)C₆H₄− | 4-(H₃CO)C₆H₄− | CH₃ | OCH₃ | |
| 47 | 2-(OCF₃)C₆H₄− | 3-Cl-4-CH₃−C₆H₃− | CH₃ | SCH₃ | 117 |

TABLE 3-continued $$R^1-SO_2-N=C(OR^2)-NH-\underset{\underset{R^4}{N}}{\overset{\underset{R^3}{N}}{\underset{\|}{\diagup}}}\text{triazine} \quad (I)$$

| Example No. | R¹ | R² | R³ | R⁴ | Melting point/[°C.] |
|---|---|---|---|---|---|
| 48 | 2-(OCHF₂)-phenyl | phenyl | CH₃ | SCH₃ | 101 |
| 49 | 2-(OCF₃)-phenyl | 2,3-dimethylphenyl | OCH₃ | OCH₃ | 100 |
| 50 | 2-(OCF₃)-phenyl | 2,3-dimethylphenyl | CH₃ | SCH₃ | 105 |
| 51 | 2-(OCHF₂)-phenyl | 2,3-dimethylphenyl | CH₃ | SCH₃ | 84 |
| 52 | 2-(OCHF₂)-phenyl | phenyl | CH₃ | OCH₃ | 130 |
| 53 | 2-(OCHF₂)-phenyl | phenyl | OCH₃ | OCH₃ | 106 |
| 54 | 2-(OCHF₂)-phenyl | phenyl | CH₃ | N(CH₃)₂ | 113 |
| 55 | 2-(OCHF₂)-phenyl | 2,3-dimethylphenyl | OCH₃ | OCH₃ | 126 |
| 56 | 2-(OCHF₂)-phenyl | phenyl | CH₃ | CH₃ | 104 |

TABLE 3-continued $$R^1-SO_2-N=C(OR^2)-NH-C(=N-)N=C(R^3)-N=C(R^4)-$$ (I)

(Structure: R¹–SO₂–N=C(OR²)–NH–C(triazine with R³ and R⁴))

| Example No. | R¹ | R² | R³ | R⁴ | Melting point/[°C.] |
|---|---|---|---|---|---|
| 57 | 2-(OCHF₂)-phenyl | 2,3-dimethylphenyl | CH₃ | N(CH₃)₂ | 141 |
| 58 | 2-biphenyl | 2,3-dimethylphenyl | OCH₃ | OCH₃ | 134 |
| 59 | 2-(OCHF₂)-phenyl | 2,3-dimethylphenyl | CH₃ | OCH₃ | 75 |
| 60 | 2-biphenyl | 2,3-dimethylphenyl | CH₃ | OCH₃ | 124 |
| 61 | 2-(OCF₃)-phenyl | 2,3-dimethylphenyl | CH₃ | N(CH₃)₂ | 147 |
| 62 | 2-(OCHF₂)-phenyl | 2-methyl-4-chlorophenyl (H₃C-, Cl-substituted phenyl) | CH₃ | OCH₃ | 130 |
| 63 | 2-biphenyl | 2,3-dimethylphenyl | CH₃ | SCH₃ | 127 |

TABLE 3-continued
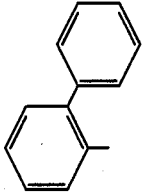
| Example No. | R¹ | R² | R³ | R⁴ | Melting point/[°C.] |
|---|---|---|---|---|---|
| 64 | 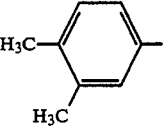 | 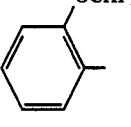 | $CH_3$ | $N(CH_3)_2$ | 171 |
| 65 | 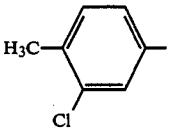 | 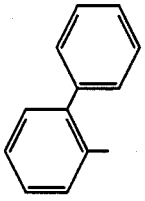 | $CH_3$ | $SCH_3$ | 98 |
| 66 | 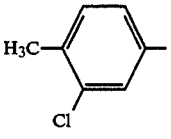 | 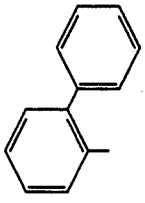 | $OCH_3$ | $OCH_3$ | 131 |
| 67 | 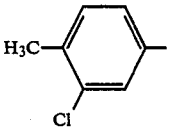 | 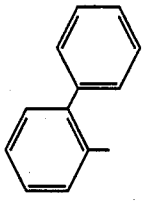 | $CH_3$ | $OCH_3$ | 117 |
| 68 | 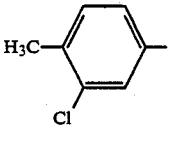 | 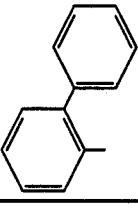 | $CH_3$ | $SCH_3$ | 118 |
| 69 | 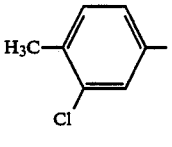 | | $CH_3$ | $N(CH_3)_2$ | 172 |

STARTING COMPOUNDS OF THE FORMULA (II)

EXAMPLE (II-1)

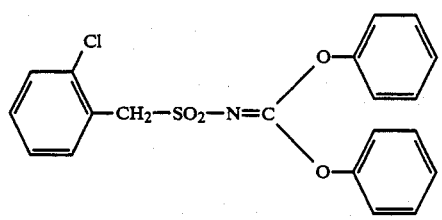

23.1 g (0.08 mol) of 2-chloro-benzylsulphonyl isocyanide dichloride are dissolved in 200 ml of acetone, and 18.8 g (0.16 mol) of sodium phenolate are added at 20° C. The exothermic reaction is cooled. The reaction mixture is stirred overnight at room temperature and then filtered with suction. The filtrate is concentrated in vacuo and the greasy residue formed slowly crystallizes completely. The crystal sludge is triturated with diisopropyl ether, filtered off with suction, washed and dried.

26.6 g (83% of theory) of O,O-diphenyl 2-chlorobenzylsulphonyliminocarbonate of melting point 130° C. are obtained.

EXAMPLE (II-2)

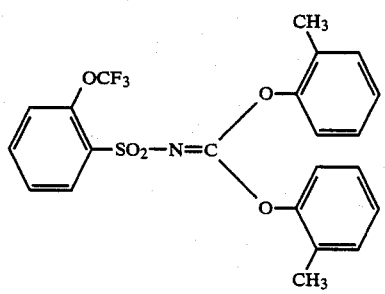

A mixture of 21.6 g (0.2 mol) of 2-methylphenol and 14 g (0.2 mol) of potassium carbonate in 200 ml of acetonitrile is heated at 80° C. for 30 minutes and cooled. 32.2 g (0.1 mol) of 2-trifluoromethoxybenzenesulphonyl isocyanide dichloride are added dropwise to this mixture such that a reaction temperature of 50° C. is not exceeded; the mixture is then subsequently stirred at 25° C. for 18 hours. The reaction mixture is diluted with 500 ml of water and extracted twice with 100 ml of methylene chloride each time. The methylene chloride solution is washed with 100 ml of 5% strength sodium hydroxide and 100 ml of water and then concentrated.

35 g (75% of theory) of O,O-di-(2-methyl-phenyl) 2-trifluoromethoxybenzenesulphonyliminocarbonate are obtained in the form of colorless crystals of melting point 95° C.

The following compounds of the formula (II) can be prepared analogously to Example (II-1) and (II-2):

TABLE 4

$$R^1-SO_2-N=C\begin{matrix}OR^2\\OR^2\end{matrix} \quad (II)$$

| Example No. | $R^1$ | $R^2$ | Physical constants |
|---|---|---|---|
| II-3 | 2,6-dichlorobenzyl (Cl, CH₂—, Cl) | phenyl | Melting point 177° C. |
| II-4 | 2-chlorobenzyl (Cl, CH₂—) | 4-nitrophenyl (O₂N—) | Melting point 185° C. |
| II-5 | 2-OCF₃-phenyl | phenyl | Melting point 112° C. |
| II-6 | 2-OCF₃-phenyl | 2,6-dichlorophenyl (Cl, Cl) | Melting point 184° C. |
| II-7 | 2-OCHF₂-phenyl | phenyl | |
| II-8 | 2-phenyl-phenyl | phenyl | |
| II-9 | 2-CON(CH₃)₂-phenyl | phenyl | |
| II-10 | 2-SO₂N(CH₃)₂-phenyl | phenyl | |
| II-11 | 2-OCHF₂-phenyl | 4-hydroxyphenyl (HO—) | |
| II-12 | 2-phenyl-phenyl | 4-hydroxyphenyl (HO—) | |
| II-13 | 2-OCF₃-phenyl | 4-hydroxyphenyl (HO—) | |
| II-14 | 2-chlorobenzyl (Cl, CH₂—) | 4-hydroxyphenyl (HO—) | |
| II-15 | 2-CON(CH₃)₂-phenyl | 4-hydroxyphenyl (HO—) | |

TABLE 4-continued $$R^1-SO_2-N=C\begin{matrix}OR^2\\OR^2\end{matrix} \qquad (II)$$

| Example No. | R¹ | R² | Physical constants |
|---|---|---|---|
| II-16 | 2-(SO₂N(CH₃)₂)-phenyl | 4-HO-phenyl | |
| II-17 | 2-Cl-benzyl | 4-Br-phenyl | |
| II-18 | 2-OCHF₂-phenyl | 4-Br-phenyl | |
| II-19 | 2-phenyl-phenyl (biphenyl) | 4-Br-phenyl | |
| II-20 | 2-OCF₃-phenyl | 4-Br-phenyl | |
| II-21 | 2-CON(CH₃)₂-phenyl | 4-Br-phenyl | |
| II-22 | 2-SO₂N(CH₃)₂-phenyl | 4-Br-phenyl | |
| II-23 | 2-Cl-benzyl | 4-H₃CO-phenyl | |
| II-24 | 2-OCHF₂-phenyl | 4-H₃CO-phenyl | |
| II-25 | 2-phenyl-phenyl | 4-H₃CO-phenyl | Wax |
| II-26 | 2-OCF₃-phenyl | 4-H₃CO-phenyl | Melting point 113° C. |
| II-27 | 2-CON(CH₃)₂-phenyl | 4-H₃CO-phenyl | |
| II-28 | 2-SO₂N(CH₃)₂-phenyl | 4-H₃CO-phenyl | |
| II-29 | 2-Cl-benzyl | 4-Cl-phenyl | |
| II-30 | 2-OCHF₂-phenyl | 4-Cl-phenyl | |
| II-31 | 2-phenyl-phenyl | 4-Cl-phenyl | |
| II-32 | 2-Cl-benzyl | 2-C₂H₅-phenyl | |
| II-33 | 2-OCF₃-phenyl | 4-Cl-phenyl | |
| II-34 | 2-CON(CH₃)₂-phenyl | 4-Cl-phenyl | |
| II-35 | 2-SO₂N(CH₃)₂-phenyl | 4-Cl-phenyl | |
| II-36 | 2-Cl-benzyl | 4-H₃CS-phenyl | |
| II-37 | 2-OCHF₂-phenyl | 4-H₃CS-phenyl | |
| II-38 | 2-phenyl-phenyl | 4-H₃CS-phenyl | |
| II-39 | 2-OCF₃-phenyl | 4-H₃CS-phenyl | |
| II-40 | 2-CON(CH₃)₂-phenyl | 4-H₃CS-phenyl | |
| II-41 | 2-SO₂N(CH₃)₂-phenyl | 4-H₃CS-phenyl | |

TABLE 4-continued $$R^1-SO_2-N=C\begin{matrix}OR^2\\OR^2\end{matrix} \quad (II)$$

| Example No. | R¹ | R² | Physical constants |
|---|---|---|---|
| II-42 | 2-Cl-C₆H₄-CH₂- | 4-CH₃-C₆H₄- | |
| II-43 | 2-OCHF₂-C₆H₄- | 4-CH₃-C₆H₄- | |
| II-44 | 2-biphenyl | 4-CH₃-C₆H₄- | Melting point 160° C. |
| II-45 | 2-OCF₃-C₆H₄- | 4-CH₃-C₆H₄- | Melting point 92–94° C. |
| II-46 | 2-CON(CH₃)₂-C₆H₄- | 4-CH₃-C₆H₄- | |
| II-47 | 2-SO₂N(CH₃)₂-C₆H₄- | 4-CH₃-C₆H₄- | |
| II-48 | 2-Cl-C₆H₄-CH₂- | 4-t-C₄H₉-C₆H₄- | 106° C. |
| II-49 | 2-OCHF₂-C₆H₄- | 4-O₂N-C₆H₄- | |
| II-50 | 2-biphenyl | 4-O₂N-C₆H₄- | |
| II-51 | 2,6-Cl₂-C₆H₃-CH₂- | 4-O₂N-C₆H₄- | |
| II-52 | 2-OCF₃-C₆H₄- | 4-t-C₄H₉-C₆H₄- | Melting point 119° C. |
| II-53 | 2-OCF₃-C₆H₄- | 4-O₂N-C₆H₄- | Melting point 154° C. |
| II-54 | 2-OCF₃-C₆H₄- | 3-NO₂-C₆H₄- | Melting point 189° C. |
| II-55 | 2-CON(CH₃)₂-C₆H₄- | 4-O₂N-C₆H₄- | |
| II-56 | 2-SO₂N(CH₃)₂-C₆H₄- | 4-O₂N-C₆H₄- | |
| II-57 | 2-Cl-C₆H₄-CH₂- | 4-C₆H₅O-C₆H₄- | |
| II-58 | 2-OCHF₂-C₆H₄- | 4-C₆H₅O-C₆H₄- | |
| II-59 | 2-biphenyl | 4-C₆H₅O-C₆H₄- | |
| II-60 | 2-OCF₃-C₆H₄- | 4-C₆H₅O-C₆H₄- | |
| II-61 | 2-CON(CH₃)₂-C₆H₄- | 4-C₆H₅O-C₆H₄- | |
| II-62 | 2-SO₂N(CH₃)₂-C₆H₄- | 4-C₆H₅O-C₆H₄- | |
| II-63 | 2-Cl-C₆H₄-CH₂- | 4-F-C₆H₄- | |
| II-64 | 2-OCHF₂-C₆H₄- | 4-F-C₆H₄- | |
| II-65 | 2-biphenyl | 4-F-C₆H₄- | |
| II-66 | 2-OCF₃-C₆H₄- | 4-F-C₆H₄- | |
| II-67 | 2-CON(CH₃)₂-C₆H₄- | 4-F-C₆H₄- | |

TABLE 4-continued $$R^1-SO_2-N=C\begin{matrix}OR^2\\OR^2\end{matrix}\qquad(II)$$

| Example No. | R¹ | R² | Physical constants |
|---|---|---|---|
| II-68 | 2-(SO₂N(CH₃)₂)-phenyl | 4-F-phenyl | |
| II-69 | 2-Cl-benzyl | 2-Cl-phenyl | |
| II-70 | 2-OCHF₂-phenyl | 2-Cl-phenyl | |
| II-71 | 2-phenyl-phenyl (biphenyl) | 2-Cl-phenyl | |
| II-72 | 2-(CON(CH₃)₂)-phenyl | 2-Cl-phenyl | |
| II-73 | 2-(SO₂N(CH₃)₂)-phenyl | 2-Cl-phenyl | |
| II-74 | 2-Cl-benzyl | 4-C₂H₅-phenyl | |
| II-75 | 2-OCHF₂-phenyl | 4-C₂H₅-phenyl | |
| II-76 | 2-phenyl-phenyl | 4-C₂H₅-phenyl | |
| II-77 | 2-OCF₃-phenyl | 4-C₂H₅-phenyl | |
| II-78 | 2-(CON(CH₃)₂)-phenyl | 4-C₂H₅-phenyl | |
| II-79 | 2-(SO₂N(CH₃)₂)-phenyl | 4-C₂H₅-phenyl | |
| II-80 | 2-OCHF₂-phenyl | 2-CH₃-phenyl | |
| II-81 | 2-phenyl-phenyl | 2-CH₃-phenyl | Wax |
| II-82 | 2-OCF₃-phenyl | 2-CH₃-phenyl | |
| II-83 | 2-Cl-benzyl | 2-CH₃-phenyl | |
| II-84 | 2-OCHF₂-phenyl | 3-CH₃-phenyl | |
| II-85 | 2-phenyl-phenyl | 3-CH₃-phenyl | Wax |
| II-86 | 2-OCF₃-phenyl | 3-CH₃-phenyl | Melting point 104° C. |
| II-87 | 2-Cl-benzyl | 3-CH₃-phenyl | |
| II-88 | 2-OCHF₂-phenyl | 3-Cl-phenyl | |
| II-89 | 2-phenyl-phenyl | 3-Cl-phenyl | |
| II-90 | 2-OCF₃-phenyl | 3-Cl-phenyl | |
| II-91 | 2-Cl-benzyl | 3-Cl-phenyl | |
| II-92 | 2-OCHF₂-phenyl | 4-i-C₃H₇-phenyl | |

TABLE 4-continued $$R^1-SO_2-N=C\begin{matrix}OR^2\\OR^2\end{matrix} \quad (II)$$

| Example No. | R¹ | R² | Physical constants |
|---|---|---|---|
| II-93 | 2-phenylphenyl | i-H₇C₃—(4-phenyl)— | |
| II-94 | 2-OCF₃-phenyl | i-H₇C₃—(4-phenyl)— | |
| II-95 | 2-Cl-benzyl (—CH₂—) | i-H₇C₃—(4-phenyl)— | |
| II-96 | 2-OCHF₂-phenyl | 2-OCH₃-phenyl | |
| II-97 | 2-phenylphenyl | 2-OCH₃-phenyl | |
| II-98 | 2-OCF₃-phenyl | 2-OCH₃-phenyl | |
| II-99 | 2-Cl-benzyl (—CH₂—) | 2-OCH₃-phenyl | |
| II-100 | 2-SCF₃-phenyl | phenyl | |
| II-101 | 2-SCF₃-phenyl | 2-OCH₃-phenyl | |
| II-102 | 2-OCHF₂-phenyl | 3-H₃CO-phenyl | |
| II-103 | 2-phenylphenyl | 3-H₃CO-phenyl | |
| II-104 | 2-OCF₃-phenyl | 3-H₃CO-phenyl | |
| II-105 | 2-Cl-benzyl (—CH₂—) | 3-H₃CO-phenyl | |
| II-106 | 2-OCHF₂-phenyl | 3-H₅C₂-phenyl | |
| II-107 | 2-phenylphenyl | 3-H₅C₂-phenyl | |
| II-108 | 2-OCF₃-phenyl | 3-H₅C₂-phenyl | |
| II-109 | 2-Cl-benzyl (—CH₂—) | 3-H₅C₂-phenyl | |
| II-110 | 2-OCHF₂-phenyl | 2-C₂H₅-phenyl | |
| II-111 | 2-phenylphenyl | 2-C₂H₅-phenyl | |
| II-112 | 2-OCF₃-phenyl | 2-C₂H₅-phenyl | |

STARTING COMPOUNDS OF THE FORMULA (IV)

EXAMPLE (IV-1)

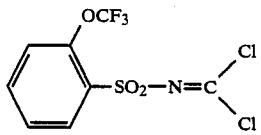

34.5 g (0.1 mol) of S,S-dimethyl 2-trifluoromethoxybenzenesulphonyl-iminodithiocarbonates are dissolved in 300 ml of carbon tetrachloride, and 8 mols of dry chlorine are added at 20° C. The reaction mixture thereby warms to about 40° C. It is subsequently stirred for 1 hour and filtered, the filtrate is concentrated in vacuo and the residue is subjected to fractional distillation in vacuo.

23.2 g (72.4% of theory) of 2-trifluoromethoxybenzenesulphonyl isocyanide dichloride of boiling point b.p. 126° C./1 mbar are thus obtained.

The compound of Example (IV-1) can also be prepared as follows:

69 g (0.2 mol) of S,S-dimethyl 2-trifluoromethoxybenzenesulphonyliminodithiocarbonate are added in portions to 418 g (3.1 mols) of sulphuryl chloride at 50° C. and the mixture is then heated under reflux for a further 3 hours. It is concentrated and the residue is distilled.

33 g (50% of theory) of 2-trifluoromethoxybenzenesulphonyl isocyanide dichloride with a boiling point b.p.: 124° C./101 Pa, are obtained.

Example (IV-2)

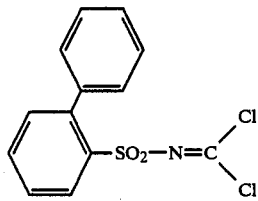

87 g (0.37 mol) of S,S-dimethyl 2-phenylbenzenesulphonyliminodithiocarbonate are added in portions to 750 g (5.55 mol of sulphuryl chloride at 50° C. When the addition has ended, the reaction mixture is heated under reflux for a further 3 hours and evaporated.

After incipient distillation, 67 g (57.9% of theory) of 2-phenylbenzenesulphonyl isocyanide dichloride are obtained in the form of a waxy substance.

The following compounds of the formula (IV) can be obtained analogously to Example (IV-1 and IV-2):

TABLE 5

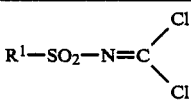

| Example No. | R¹ | Physical constants |
|---|---|---|
| IV-3 | 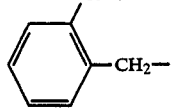 | Melting point 79° C. |
| IV-4 | 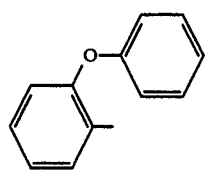 | |
| IV-5 | 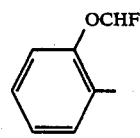 OCHF₂ | Boiling point 151° C./101 Pa. |
| IV-6 | 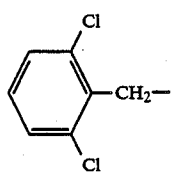 | Melting point 94° C. |

TABLE 5-continued

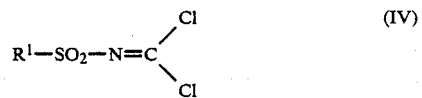

| Example No. | R¹ | Physical constants |
|---|---|---|
| IV-7 | 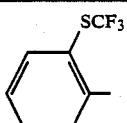 SCF₃ | |

STARTING COMPOUNDS OF THE FORMULA (VI)

Example (VI-1)

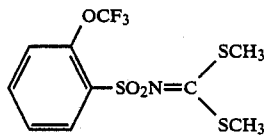

A mixture of 240 g (1 mol) of 2-trifluoromethoxybenzenesulphonamide, 1,500 ml of dimethylformamide and 85 g (1.11 mols) of carbon disulphide is cooled to 5° C. and a solution of 80 g (2 mols) of sodium hydroxide in 150 ml of water is added such that a reaction temperature of 10° C. is not exceeded. The mixture is then stirred at 5° C.–10° C. for a further 30 minutes, 284 g (2 mols) of methyl iodide are added dropwise and the mixture is subsequently stirred at 20° C.–25° C. for 18 hours. The reaction mixture is poured into 5 l of water and the reaction product which has precipitated out is filtered off. The residue on the filter is taken up in 1.5 l of methylene chloride, the mixture is filtered and the filtrate is dried over sodium sulphate and concentrated. The residue is triturated with petroleum ether.

261 g (85% of theory) of S,S-dimethyl 2-trifluoromethoxybenzenesulphonyliminodithiocarbonate of melting point 107° C. are obtained.

The compounds listed in the following Table 6 can be prepared analogously to Example (VI-1):

TABLE 6

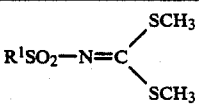

| Example No. | R¹ | Melting point/[°C.] |
|---|---|---|
| VI-2 | 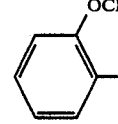 OCHF₂ | 103 |

TABLE 6-continued $$R^1SO_2-N=C\begin{smallmatrix}SCH_3\\SCH_3\end{smallmatrix} \quad (VI)$$

| Example No. | $R^1$ | Melting point/[°C] |
|---|---|---|
| VI-3 | biphenyl-2-yl | 117 |
| VI-4 | 2-(SO$_2$N(CH$_3$)$_2$)-phenyl | |
| VI-5 | 2-(SO$_2$CH$_3$)-phenyl | |
| VI-6 | 2-(SO$_2$N(CH$_3$)(OCH$_3$))-phenyl | |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison with the development of the untreated control. The figures denote:

0% = no action (like untreated control)
100% = total destruction

In this test, the compound (20) of the preparation examples exhibits a better herbicidal action against weeds, such as, for example, Datura, Ipomoea, Portulak, Sinapis and Alopecurus, in crops such as, for example, wheat, than comparison compound (A). (A)=N'-(2-chlorobenzenesulphonyl)-N''-(4,6-dimethyl-1,3,5-triazin-2-yl)-O-phenyl-isourea (known from European Pat. No. A-173,957).

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compound (20) of the preparation examples exhibits a better herbicidal action against weeds, such as, for example, Cassia, Datura, Matricaria, Sida, Stellaria and Agropyron, in crops such as, for example, wheat, than comparison compounds (A) and (B). (B)=N'-(2-chloro-benzenesulphonyl)-N''-(4,6-dimethylpyrimidin-2-yl)-O-(4-chlorophenyl)-isourea (known from Swiss Patent Specification No. 646,957).

It is understood that the specification and examples are illustrative but not limitative of the present invention and that other embodiments within the spirit and scope of the invention will suggest themselves to those skilled in the art.

We claim:

1. An O-aryl-N'-(triazin-2-yl)-isourea of the formula

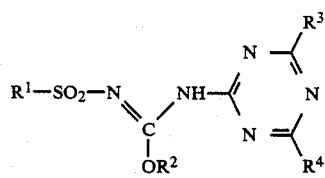

in which
$R^1$ represents the radical

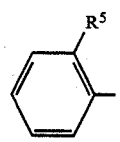

wherein
$R^5$ represents trifluromethoxy, difluoromethoxy, phenyl, phenoxy, trifluoromethylthio, difluoromethylthio, di-($C_1$–$C_4$-alkyl)-aminocarbonyl, $C_1$–$C_4$-alkylsulphonyl, $C_1$–$C_4$-alkoxyaminosulphonyl, N-($C_1$–$C_4$-alkoxy)-N-($C_1$–$C_4$-alkyl)aminosulphonyl, $C_1$–$C_4$-alkylaminosulphonyl or di-($C_1$–$C_4$-alkyl)-aminosulphonyl,
or wherein
$R^1$ represents the radical

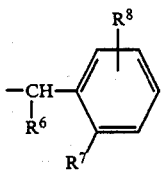

wherein
R⁶ represents hydrogen or $C_1$–$C_4$-alkyl and
R⁷ and R⁸ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxycarbonyl, $C_1$–$C_4$-alkylsulphonyl or di-($C_1$–$C_4$-alkyl)-aminosulphonyl;

R² represents a phenyl radical which is optionally substituted by one or more radicals from the series comprising halogen, cyano, nitro, hydroxyl, carboxyl, $C_1$–$C_6$-alkyl (which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl), $C_3$–$C_6$-cycloalkyl, $C_1$–$C_4$-alkoxy (which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl), $C_1$–$C_4$-alkylthio (which is optionally substituted by fluorine, chlorine, bromine, cyano, carboxyl, $C_1$–$C_4$-alkoxy-carbonyl), amino, $C_1$–$C_4$-alkyl-amino and di-($C_1$–$C_4$-alkyl)-amino (which are optionally substituted by fluorine, chlorine, bromine, cyano, carboxyl, $C_1$–$C_4$-alkoxy or $C_1$–$C_4$-alkoxy-carbonyl), $C_1$–$C_4$-alkyl-carbonylamino, $C_1$–$C_4$-alkoxycarbonylamino, (di)-$C_1$–$C_4$-alkylamino-carbonylamino, formyl, $C_1$–$C_4$-alkyl-carbonyl, benzoyl, $C_1$–$C_4$-alkoxy-carbonyl, phenoxy-carbonyl, benzyloxycarbonyl, phenyl (which is optionally substituted by fluorine, chlorine, bromine, cyano, nitro, hydroxyl or methyl), phenoxy, phenylthio, phenylsulphonyl, phenylamino or phenylazo (which are optionally substituted by fluorine, chlorine, bromine, cyano, nitro, methyl and/or trifluoromethyl), pyridoxy and pyrimidoxy (which are optionally substituted by fluorine, chlorine, bromine, cyano, nitro, methyl and/or trifluoromethyl), $C_1$–$C_4$-alkyl-carbonyloxy, $C_1$–$C_4$-alkoxycarbonyloxy, $C_1$–$C_4$-alkyl-aminocarbonyloxy and di-($C_1$–$C_4$-alkyl)-amino-carbonyloxy, or which is optionally fused with a benzo radical (which is optionally substituted by fluorine, chlorine, bromine, cyano, nitro, methyl and/or trifluoromethyl, R³ represents hydrogen, halogen, hydroxyl, $C_1$–$C_6$-alkylamino or di-($C_1$–$C_6$-alkyl-amino, or represents $C_1$–$C_6$-alkyl, $C_1$–$C_6$-alkoxy or $C_1$–$C_6$-alkylthio each of which is optionally substituted by fluorine and/or chlorine, and R⁴ represents hydrogen, halogen or hydroxyl, or represents optionally substituted $C_1$–$C_6$-alkyl, $C_1$–$C_6$-alkoxy or $C_1$–$C_6$-alkylthio, or represents $C_1$–$C_6$-alkylamino or di-($C_1$–$C_6$-alkyl)-amino.

2. An O-aryl-N'-(triazin-2-yl)-isourea according to claim 1,
in which
R¹ represents the radical

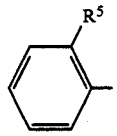

wherein
R⁵ represents trifluoromethoxy, difluoromethoxy, phenyl, phenoxy, trifluoromethylthio, difluoromethylthio, di-($C_1$–$C_4$-alkyl)-aminocarbonyl, $C_1$–$C_3$-alkylsulphonyl, $C_1$–$C_4$-alkoxyaminosulphonyl, N-($C_1$–$C_2$-alkoxy)-N-($C_1$–$C_2$-alkyl)-aminosulphonyl, $C_1$–$C_2$-alkylaminosulphonyl or di-($C_1$–$C_2$-alkyl)-aminosulphonyl,
or wherein
R¹ represents the radical

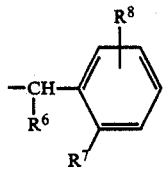

wherein
R⁶ represents hydrogen or $C_1$–$C_4$-alkyl and
R⁷ and R⁸ are identical or different and represent hydrogen, fluorine, chlorine, bromine, cyano, methyl, methoxy, trifluoromethyl, trifluoromethoxy, difluoromethoxy, carboxyl, methoxycarbonyl, ethoxycarbonyl, methylsulphonyl, ethylsulphonyl, dimethylaminosulphonyl or diethylaminosulphonyl;
and wherein
R² represents a phenyl radical which is optionally substituted by one or more radicals from the series comprising halogen, cyano, nitro, hydroxyl, carboxyl, $C_1$–$C_6$-alkyl (which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl), $C_3$–$C_6$-cycloalkyl, $C_1$–$C_4$-alkoxy (which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl), $C_1$–$C_4$-alkylthio (which is optionally substituted by fluorine, chlorine, bromine, cyano, carboxyl, $C_1$–$C_4$-alkoxy-carbonyl), amino, $C_1$–$C_4$-alkyl-amino and di-($C_1$–$C_4$-alkyl)-amino (which are optionally sustituted by fluorine, chlorine, bromine, cyano, carboxyl, $C_1$–$C_4$-alkoxy or $C_1$–$C_4$-alkoxy-carbonyl), $C_1$–$C_4$-alkyl-carbonylamino, $C_1$–$C_4$-alkoxy-carbonylamino, (di)-$C_1$–$C_4$-alkylamino-carbonylamino, formyl, $C_1$–$C_4$-alkyl-carbonyl, benzoyl, $C_1$–$C_4$-alkoxy-carbonyl, phenoxy-carbonyl, benzyloxycarbonyl, phenyl (which is optionally substituted by fluorine, chlorine, bromine, cyano, nitro, hydroxyl or methyl), phenoxy, phenylthio, phenylsulphonyl, phenylamino or phenylazo (which are optionally substituted by fluorine, chlorine, bromine, cyano, nitro, methyl and/or trifluoromethyl), pyridoxy and pyrimidoxy (which are optionally substituted by fluorine, chlorine, bromine, cyano, nitro, methyl and/or trifluoromethyl), $C_1$–$C_4$-alkyl-carbonyloxy, $C_1$–$C_4$-alkoxy-carbonyloxy, $C_1$–$C_4$-alkyl-aminocarbonyloxy and di-($C_1$-$C_4$-alkyl)-amino-carbonyloxy, or which is optionally fused with a benzo radical (which is optionally substituted by fluorine, chlorine, bromine, cyano, nitro, methyl and/or trifluoromethyl);

and wherein $R^3$ represents hydrogen, fluorine, chlorine, bromine, hydroxyl, $C_1$-$C_4$-alkylamino, di-($C_1$-$C_4$-alkyl)-amino, $C_1$-$C_4$-alkyl (which is optionally substituted by fluorine and/or chlorine), $C_1$-$C_4$-alkoxy (which is optionally substituted by fluorine and/or chlorine) or $C_1$-$C_4$-alkylthio (which is optionally substituted by fluorine and/or chlorine) and $R^4$ represents hydrogen, fluorine, chlorine, bromine, hydroxyl, $C_1$-$C_4$-alkyl (which is optionally substituted by fluorine and/or chlorine), $C_1$-$C_4$-alkoxy (which is optionally substituted by fluorine and/or chlorine), $C_1$-$C_4$-alkylthio (which is optionally substituted by fluorine and/or chlorine), $C_1$-$C_4$-alkyl-amino or di-($C_1$-$C_4$-alkyl)-amino.

3. An O-aryl-$N'$-(triazin-2-yl)-isourea according to claim 1,
in which
$R^1$ represents the radical

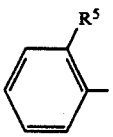

wherein $R^5$ represents difluoromethoxy, trifluoromethoxy, difluoromethylthio, trifluoromethylthio, dimethylaminocarbonyl, diethylaminocarbonyl, di-n-propylaminocarbonyl, methylsulphonyl, ethylsulphonyl, n-propylsulphonyl, i-propylsulphonyl, dimethylaminosulphonyl, diethylaminosulphonyl, methoxyaminosulphonyl, N-methoxy-N-methylaminosulphonyl or phenyl, or represents phenoxy, $R^2$ represents a phenyl radical which is optionally substituted by one or two radicals from the series comprising fluorine, chlorine, bromine, iodine, cyano, nitro, hydroxyl, carboxyl, $C_1$-$C_3$-alkoxycarbonyl, $C_1$-$C_4$-alkyl, trifluoromethyl, hydroxymethyl, methoxycarbonylmethyl, phenyl-$C_1$-$C_3$-alkyl, cyclohexyl, $C_1$-$C_3$-alkoxy, trifluoromethoxy, $C_1$-$C_3$-alkylthio, trifluoromethylthio, dimethylamino, amino, acetylamino, methylaminocarbonyl, formyl, acetyl, benzoyl, phenyl, hydroxyphenyl, phenoxy (which is optionally substituted by chlorine and/or trifluoromethyl), phenylamino, phenylazo and pyridoxy (which is optionally substituted by chlorine and/or trifluoromethyl), or which is optionally benzofused;

$R^3$ represents fluorine, chlorine, methyl, ethyl, methoxy, ethoxy, methylthio, ethylthio, methylamino, ethylamino, dimethylamino or diethylamino, and $R^4$ represents fluorine, chlorine, methyl, ethyl, methoxy, ethoxy, methylthio, ethylthio, methylamino, ethylamino, dimethylamino or diethylamino.

4. A compound according to claim 1, wherein such compound is $N'$-(4,6-dimethoxy-1,3,5-triazin-2-yl)-$N''$-(2-trifluoromethoxybenzenesulphonyl)-O-phenylisourea of the formula

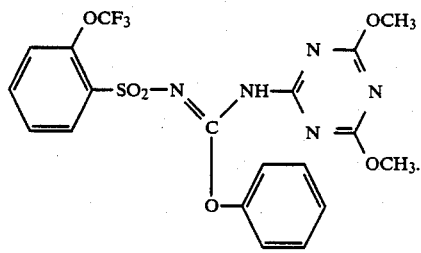

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

* * * * *